United States Patent [19]

Lago et al.

[11] Patent Number: 5,371,312
[45] Date of Patent: Dec. 6, 1994

[54] SHAPE SELECTIVE HYDROCARBON CONVERSIONS OVER MODIFIED CATALYST

[75] Inventors: Rudolph M. Lago, Yardley, Pa.;
David O. Marler, Deptford, N.J.;
Sharon B. McCullen, Newtown, Pa.;
David H. Olson, Pennington, N.J.

[73] Assignee: Mobil Oil Corp., Fairfax, Va.

[21] Appl. No.: 42,430

[22] Filed: Apr. 5, 1993

[51] Int. Cl.⁵ .................................. C07C 5/52
[52] U.S. Cl. ......................... 585/475; 585/407; 585/467; 585/469; 585/638; 585/733
[58] Field of Search ............. 585/407, 467, 469, 475, 585/638, 733

[56] References Cited

U.S. PATENT DOCUMENTS

| | | | |
|---|---|---|---|
| 3,682,996 | 8/1972 | Kerr | 260/448 C |
| 3,698,157 | 10/1972 | Allen et al. | 55/67 |
| 4,060,568 | 11/1977 | Rodewald | 260/682 |
| 4,090,981 | 5/1978 | Rodewald | 252/455 Z |
| 4,100,215 | 7/1978 | Chen | 260/671 M |
| 4,127,616 | 11/1978 | Rodewald | 260/671 R |
| 4,145,315 | 3/1979 | Rodewald | 252/455 Z |
| 4,283,306 | 8/1981 | Herkes | 252/432 |
| 4,447,583 | 10/1984 | Rodewald | 502/71 |
| 4,465,886 | 8/1984 | Rodewald | 585/467 |
| 4,843,057 | 6/1989 | D'Amore | 502/263 |
| 4,851,604 | 7/1989 | Absil et al. | 585/475 |
| 4,927,979 | 5/1990 | Yamagishi et al. | 568/791 |
| 4,950,853 | 8/1990 | Wang et al. | 585/467 |

FOREIGN PATENT DOCUMENTS 296582 12/1988 European Pat. Off. .
062739 3/1987 Japan .

OTHER PUBLICATIONS

Hibino, et al., Journal of Catalysis, 12, 551–558 (1991) Shape-Selectivity Over HZSM-5 Modified by Chemical Vapor Deposition of Silicone alkoxide.

Primary Examiner—Asok Pal
Assistant Examiner—P. Achutamurthy
Attorney, Agent, or Firm—Alexander J. McKillop; Dennis P. Santini; Edward F. Kenehan

[57] ABSTRACT

A process for shape selective hydrocarbon conversion involves contacting a hydrocarbon feedstream under conversion conditions with a catalytic molecular sieve which has been modified by treatment with an amino silane polymer while molecular sieve acid sites are protected. When the process is toluene disproportionation, a toluene feedstream may also contain a second silicon source which is a high pxylene selectivating agent. The invention also includes the modification method and the shape selective catalyst which results from the modification.

22 Claims, No Drawings

SHAPE SELECTIVE HYDROCARBON CONVERSIONS OVER MODIFIED CATALYST

BACKGROUND OF THE INVENTION

1. Field of the Invention

The present invention is directed to a shape selective hydrocarbon conversion over a modified catalyst. The invention is also directed to a method for modifying the catalyst and the modified catalyst. A catalytic molecular sieve having protected acid sites is modified for shape selectivity by treatment with an amino silane polymer.

2. Description of the Prior Art

The term shape-selective catalysis describes unexpected catalytic selectivities in zeolites. The principles behind shape selective catalysis have been reviewed extensively, e.g. by N.Y. Chen, W.E. Garwood and F.G. Dwyer, "Shape Selective Catalysis in Industrial Applications, 36, Marcel Dekker, Inc. (1989). Within a zeolite pore, hydrocarbon conversion reactions such as paraffin isomerization, olefin skeletal or double bond isomerization, oligomerization and aromatic disproportionation, alkylation or transalkylation reactions are governed by constraints imposed by the channel size. Reactant selectivity occurs when a fraction of the feedstock is too large to enter the zeolite pores to react; while product selectivity occurs when some of the products cannot leave the zeolite channels. Product distributions can also be altered by transition state selectivity in which certain reactions cannot occur because the reaction transition state is too large to form within the zeolite pores or cages. A final type of selectivity results from configurational diffusion where the dimensions of the molecule approach that of the zeolite pore system. A small change in dimensions of the molecule or the zeolite pore can result in large diffusion changes leading to different product distributions. This type of shape selective catalysis is demonstrated, for example, in selective toluene disproportionation to p-xylene.

Para-xylene is a product of xylene isomerization in commercial operations. Para-xylene may also be produced by methylation of toluene over a catalyst under conversion conditions. Examples are the reaction of toluene with methanol as described by Chen et al., J. Amer. Chem. Sec. 1979, 101, 6783, and toluene disproportionation, as described by Pines in "The Chemistry of Catalytic Hydrocarbon Conversions", Academic Press, N.Y., 1981, p. 72. Such methods typically result in the production of a mixture including para-xylene, ortho-xylene, and meta-xylene at their relative equilibrium concentration. A concentration of p-xylene above equilibrium concentration can be obtained depending upon the para-selectivity of the catalyst and the reaction conditions. The yield, i.e., the amount of feedstock actually converted to xylene, is also affected by the catalyst and the reaction conditions. The equilibrium reaction for the conversion of toluene to xylene and benzene proceeds as follows:

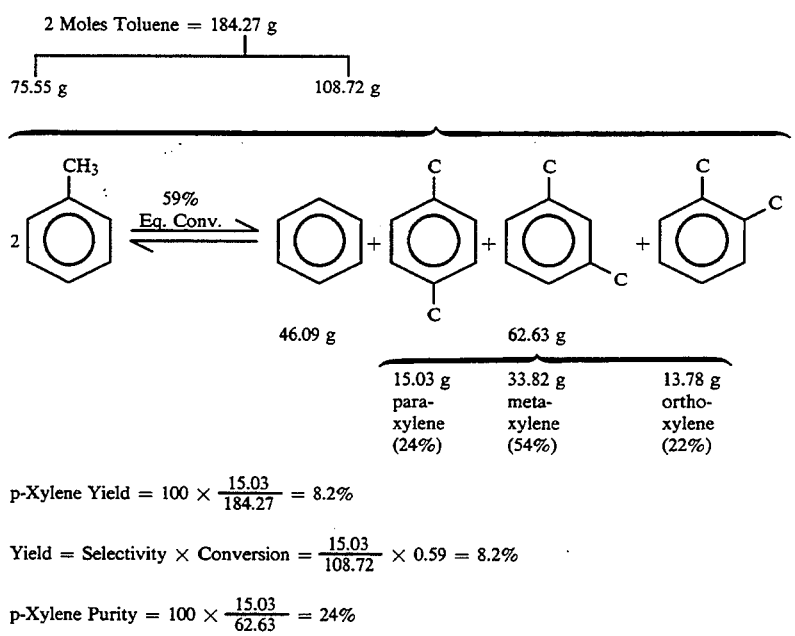

$$\text{p-Xylene Yield} = 100 \times \frac{15.03}{184.27} = 8.2\%$$

$$\text{Yield} = \text{Selectivity} \times \text{Conversion} = \frac{15.03}{108.72} \times 0.59 = 8.2\%$$

$$\text{p-Xylene Purity} = 100 \times \frac{15.03}{62.63} = 24\%$$

One method for increasing selectivity of zeolite catalysts is to modify the catalyst by treatment with "selectivating agents". Various silicon compounds have been used to modify catalysts which are in the hydrogen form to improve selectivity in hydrocarbon conversion processes. For example, U.S. Pat. Nos. 4,145,315, 4,127,616 and 4,090,981 describe the use of a silicone compound dissolved in an organic solvent to treat a hydrogen form of a zeolite. U.S. Pat. Nos. 4,465,886 and 4,477,583 describe the use of an aqueous emulsion of a silicone to treat the hydrogen form of a zeolite. U.S. Pat. Nos. 4,950,835 and 4,927,979 describe the use of alkoxysilanes to treat a hydrogen form of a zeolite. U.S. Pat. Nos. 4,100,215 and 3,698,157 describe the use of silanes to treat a hydrogen form of a zeolite.

There has been no suggestion, however, to modify a zeolite having protected acid sites which may therefore be modified in as-synthesized form, by contacting with an amino silane polymer to provide a zeolite with enhanced shape selectivity.

Accordingly, it is an object of the invention to improve selectivity in catalytic molecular sieves thereby improving shape selectivity in hydrocarbon conversion processes over the molecular sieves.

SUMMARY OF THE INVENTION

The invention is a process for a shape selective hydrocarbon conversion by contacting a feedstream comprising the hydrocarbon to be converted with a catalytic molecular sieve which has been modified by pre-selectivation with an amino silane polymer. During pre-selectivation, the acid sites of the zeolite are protected.

The invention is also a process for disproportionation of toluene into xylene which comprises contacting a reaction stream comprising toluene, at reaction conditions for converting toluene to xylene, with a catalytic molecular sieve which has been modified by first being preselectivated with a first silicon source that is an amino silane polymer. The reaction stream may also contain a second silicon source which is a high-efficiency para-xylene selectivating agent to provide a single-pass para-xylene selectivity, relative to all xylene product, of at least about 90% with at least 15% toluene conversion.

The invention is also a method for modifying a catalytic molecular sieve which includes contacting a molecular sieve having a Constraint Index of 1 to 12 with an aqueous solution of an amino silane polymer and calcining. The molecular sieve may be subsequently contacted with a mixture of a second silicon source which is a high efficiency para-xylene selectivating agent and toluene at reaction conditions for converting toluene to xylene to provide a catalyst with greatly enhanced para-selectivity.

The invention is also a molecular sieve having an initial Constraint Index of 1–12 which is modified by contacting with an amino silane polymer, calcining, and which may be subsequently contacted with a mixture of a high-efficiency, para-xylene selectivating agent and toluene at reaction conditions for converting toluene to xylene.

Advantageously, the modified catalyst has enhanced shape selectivity for hydrocarbon conversions. Accordingly, the toluene disproportionation process of this invention has increased selectivity for para-xylene.

DETAILED DESCRIPTION OF THE INVENTION

The present invention is useful in shape selective hydrocarbon conversion reactions, for example, in converting various aromatics such as toluene to commercially useful para-substituted benzenes, such as para-xylene.

Molecular sieves to be used in the process of the invention include intermediate pore zeolites. Such medium pore zeolites are considered to have a Constraint Index from about 1 to about 12. The method by which Constraint Index is determined is described fully in U.S. Pat. No. 4,016,218, incorporated herein by reference. Zeolites which conform to the specified values of Constraint Index for intermediate pore zeolites include, for example, ZSM-5, ZSM-11, ZSM-5/ZSM-11 intermediate, ZSM-12, ZSM-22, ZSM-23, ZSM-35, ZSM-48, ZSM-50 and ZSM-57 which are described for example, in U.S. Pat. Nos. 3,702,886 and Re. No. 29,949, 3,709,979, 4,229,424, 3,832,449, 4,556,447, 4,076,842, 4,016,245, 4,046,859, 4,397,827, 4,973,781 and EP 127,399 to which reference is made for details of these zeolites. These zeolites may be produced with differing silica:alumina ratios ranging from 12:1 upwards. They may, in fact, be produced from reaction mixtures from which aluminum is intentionally excluded, so as to produce materials having extremely high silica:alumina ratios which, in theory at least may extend up to infinity. Silica:alumina ratios of at least 20:1 and higher will be common for these zeolites, e.g., 24:1, 70:1, 200:1, 500:1, 600:1 or even higher. MCM-22, described in U.S. Pat. No. 4,973,784, is also useful herein.

Zeolites to be used herein preferably have a silica/alumina ratio from about 10 to about 200. Preferred intermediate pore zeolites include ZSM-5, ZSM-11, ZSM-12, and ZSM-35.

In the synthesis of these zeolites, a reaction mixture is prepared generally containing an oxide of silicon, optionally an aluminum source, a templating agent which is an organic nitrogen containing compound, and an alkaline aqueous medium.

The silicon oxide can be supplied from known sources such as silicates, silica hydrosol, precipitated silica hydrosol, precipitated silica, e.g. Hi-Sil, silica gel, silica acid. The aluminum oxide may be provided as only an impurity in another reactant, e.g., the silica source.

The sources of organic nitrogen-containing cations, depending, of course, on the particular zeolite product to result from crystallization from the reaction mixture, may be primary, secondary or tertiary amines or quaternary ammonium compounds. Non-limiting examples of quaternary ammonium compounds include salts of tetramethylammonium, tetraethylammonium, tetrapropylammonium, tetrabutylammonium, diethylammonium, triethylammonium, dibenzylammonium, dibenzyldimethylammonium, dibenzyldiethylammonium, benzyltrimethylammonium, tetrabutylphosphonium and chlorine. Non-limiting examples of amines useful herein as organic directing agents in zeolite synthesis include the compounds of trimethylamine, triethylamine, tripropylamine, ethylenediamine, propanediamine, butanediamine, pentanediamine, hexanediamine, methylamine, ethylamine, ethyldiamine, propylamine, butylamine, diamethylamine, diethylamine, dipropylamine, benzylamine, aniline, pyridine, piperidine and pyrrolidine or 2-(hydroxylalkyl-triammonium compounds.

The sources of alkali or alkaline earth metal oxide may be, for example, sodium, lithium, calcium, magnesium, cesium or potassium hydroxides, halides (e.g. chlorides, and bromides), sulfates, nitrates, acetates, silicates, aluminates, phosphates and salts of carboxylic acids.

Because of the composition of the synthesis mixture, the as-synthesized zeolites may contain alkali or alkaline earth metal ions and/or organic nitrogen-containing cations. The organic cations are generally removed by calcination or other methods known in the art. Before subsequent treatment or use of the catalyst, the alkali or alkaline earth metals have conventionally been removed and the zeolite converted to the hydrogen form, often by intermediate formation of the ammonium form by ion exchange and calcination of the ammonium form to yield the hydrogen form. In the present invention, however, the catalyst includes alkali or alkaline earth metal cations and/or organic cations associated with active sites during pre-selectivation treatment. Therefore, the catalyst can be modified in an as-synthesized form.

The activity of the zeolite is an important consideration in acid-type catalysis such as toluene disproportionation. Silicious zeolites may be considered contain SiO$_4$-tetrahedra. Substitution for the tetravalent element by a trivalent element such as aluminum produces a negative charge which must be balanced. If this is done by a proton, the material is acidic. The activity of the catalyst may be described in terms of its Alpha Value.

The Alpha Value is an approximate indication of the catalytic cracking activity of the catalyst compared to a standard catalyst and it gives the relative rate constant (rate of normal hexane conversion per volume of catalyst per unit time.) It is based on the activity of the amorphous silica-alumina cracking catalyst taken as an Alpha of 1 (Rate Constant=0.016 sec$^{-1}$). The Alpha Test is described in U.S. Pat. 3,354,078 and in The Journal of Catalysis, vol. 4, pp. 522–529 (August 1965): Vol. 6, p. 278 (1966); and Vol. 61, p. 395 (1980), each incorporated herein by reference as to that description. It is noted that intrinsic rate constants for many acid-catalyzed reactions are proportional to the Alpha Value for a particular crystalline silicate catalyst (see "The Active Site of Acidic Aluminosilicate Catalysts," Nature Vol 309, No. 5959, pp. 589–591, 14 June 1984). The experimental conditions of the test used herein include a constant temperature of 538° C. and a variable flow rate as described in detail in the Journal of Catalysis, Vol. 61, p. 395.

In the invention, the catalyst preferably has an alpha value greater than 2, for example about 50-2000, and a silica-alumina ratio less than 10,000 preferably about 10-500. The Alpha Value of the catalyst may be increased by treating the catalyst with nitric acid or by mild steaming as discussed in U.S. Pat. No. 4,326,994.

Since acid-type catalysis such as toluene disproportionation requires a catalyst having inherent acid activity, i.e., an elevated alpha, modifications of the catalyst should not reduce the internal acid sites. While it is not intended to be bound by theory, it is believed that activity loss during catalyst silicon modification occurs through dealumination. Using the modification method described herein, dealumination can be minimized.

It has now been found that an improved catalyst modification method results when zeolite acid sites are protected while a first silicon-containing compound which is an amino silane polymer is used to modify the catalyst to increase selectivity.

The amino silanes useful herein are water soluble and may be represented by the formula:

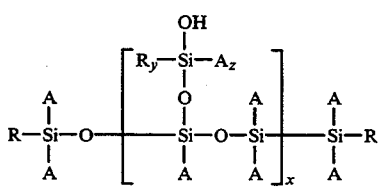

wherein
R is a C$_{1-6}$ alkane
A is ethylamine, n-propylamine, iso-propylamine, n-butylamine or iso-butylamine
x is 1–50
y is 0–2
z is 0–2
y+z=2

The silane polymer is preferably diluted in an aqueous solution in a silane polymer/H$_2$O weight ratio of from about 100/1 to about 1/1000.

Amino silanes useful herein are commercially available as Hydrosils manufactured by Hüls, America.

The zeolite catalyst to be treated is preferably in the alkali or alkaline earth metal form and/or contains organic cations such as the amines or quaternary ammonium compounds described above. Alkali metals include lithium, sodium, potassium, rubidium, cesium and francium. Alkaline earth metals include calcium, barium, strontium and radium. Particularly preferred is sodium. The zeolite may be in an as-synthesized form or it may be exchanged into the alkali alkaline earth metal or organic cation form by ion exchange. The catalyst to be treated may be incorporated with a binder or unbound.

The catalyst is contacted with a substantially aqueous solution of the silane polymer at a catalyst/polymer solution ratio of from about 10 to about 0.001 at a temperature of about 10° C. to about 100° C., for a time of about 1 hour to about 25 hours, then calcined. Modes of treatment include, for example, impregnation and excess solution exchange.

Following deposition of the first silicon-containing compound, the catalyst is calcined. For example, the catalyst may be calcined in an oxygen-containing atmosphere, preferably air, at a rate of 0.2° to 5° C./minute to a temperature greater than 300° C. but below a temperature at which the crystallinity of the zeolite is adversely affected. Generally, such temperature will be below 600° C. Preferably, the temperature of calcination is within the approximate range of 350° to 550° C. The product is maintained at the calcination temperature usually for 1 to 24 hours.

The modified molecular sieve, with or without binder, shows improved selectivity in shape selective hydrocarbon conversion processes.

Shape Selective Conversions

Zeolites modified in accordance with the invention are generally useful as catalysts in shape selective hydrocarbon conversion processes including cracking reactions involving dewaxing of hydrocarbon feedstocks; isomerization of alkylaromatics; transalkylation of alkylaromatics; oligomerization of olefins to form gasoline, distillate, lube oils or chemicals; alkylation of aromatics; conversion of aromatics to dialkyl-substituted benzene; conversion of oxygenates to hydrocarbons; and conversion of light paraffins and olefins to aromatics.

Dewaxing

The subject catalysts have good cracking and hydrocracking activity and may be used to convert paraffins from high to low molecular weight substances in dewaxing processes. The catalysts of the invention may be used in processes such as those described, for example, in U.S. Pat. Nos. 3,700,585, Re. 28,398, 3,968,024 and 4,181,598 which are incorporated herein by references. The term dewaxing means the removal of those hydrocarbons which will readily solidify (waxes) from petroleum stocks. Hydrocarbon feeds which can be treated include lubricating oil stocks as well as those which have a freeze point or pour point problem, i.e., petroleum stocks boiling above 350° F. The dewaxing can be carried out at either cracking or hydrocracking conditions.

In U.S. Pat. No. 3,700,585 and Re. 28,398 to Chen et al., typical cracking conditions include a liquid hourly space velocity (LHSV) between about 0.5 and 200, a temperature between about 280° C. (550° F.) and 590° C. (1100° F.), a pressure between about subatmospheric and several hundred atmospheres over ZSM-5 type catalysts. Typical hydrocracking conditions include a liquid hourly space velocity between about 0.1 and 10, a temperature between about 340° C. (650° F) and 538° (1000° F), a pressure between about 100 and 3000 psig, and a hydrogen to hydrocarbon mole ratio between about one and 20. U.S. Pat. No. 3,968,024 describes similar conversions using ZSM-5 of small crystal size. U.S. Pat. No. 4,181,598 describes shape selective cracking to produce lubes.

Isomerization of alkylaromatics

The modified catalysts of the invention are also advantageously used in the isomerization of alkylaromatics in conversion reactions of the type described, for example, in U.S. Pat. Nos. 3,856,872, 3,856,873, Re. 30,157, 4,101,595, 4,101,597, 4,312,790, Re. 31,919 and 4,224,141 which are herein incorporated by reference.

In U.S. Pat. No. 3,856,872 to Morrison, there is described a process for converting $C_8$ aromatics xylene and ethylbenzene to para-xylene (octafining) at a temperature of 550° F. (288° C.) to 900° F. (482° C.), a pressure of 150 to 300 psig, and a liquid hour space velocity (LHSV) of 1 to 200 over an acid form catalyst containing metal such as platinum or nickel and hydrogen.

In U.S. Pat. No. 3,856,873 to Burress, mixtures of $C_8$ aromatic hydrocarbons are isomerized to para-xylene by contact in vapor phase with zeolite at a temperature of 500° F. (260° C.) to 1000° F. (538° C.), a pressure of 0 (atmospheric) to 1,000 psig, and a WHSV of 0.5 to 250 with no added hydrogen. The catalyst can be an acid ZSM-5 or ZSM-12.

U.S. Pat. No. 4,101,595 to Chen et al. describes the production of para-xylene from aromatics of 8 to 10 carbons over a dual function catalyst with a shape selective acid catalyzed step at a temperature of 650° F. (343° C.) to 1000° F. (538° C.), a pressure of 50 to 500 psig, a LHSV of 0.1 to 100 and a molar of hydrogen/hydrocarbon of 0.1 to 15. The acid form catalyst has a Constraint Index of 1 to 12, a silica/alumina ratio of at least 12, a crystal density of not less than 1.6 g/cc, may be precoked, and includes Group VIII noble metal.

In U.S. Pat. No. 4,101,597 to Breckenridge, a $C_8$ feed is first isomerized at 550° F. (288° C.) to 700° F. (371° C.) over a zeolite having a Constraint Index of 1 to 12, a silica/alumina ratio of at least 12 and containing a metal having a hydrogenation/dehydrogenation function. A $C^{9+}$ fraction produced during isomerization of $C_8$ is separated from the other isomerization products, blended with hydrogen and toluene and contacted with a porous, acidic catalyst such as ZSM-5 at 750° F. (399° C.) to 900° F. (482° C.). The catalyst has a Constraint Index of 1 to 12, a silica/alumina ratio of at least 12, and a metal providing hydrogenation/dehydrogenation function.

In U.S. Pat. No. 4,224,141 to Morrison, $C_8$ aromatics are isomerized to benzene, toluene and xylenes over a ZSM-5 which is reduced in activity by dilution with inert matrix, steaming or thermal treatment, very high silica/alumina ratio, base exchange with alkali metal, coking or the like. The conversion is at a temperature of 800° F. (427° C.) to 1000° F. (538° C.) in a low pressure isomerization unit at a pressure only sufficient to overcome pressure drop through downstream processing equipment, e.g. below 100 psig, and a WHSV of 1 to 200.

In U.S. Pat. No. 4,312,790 and Re. 31,919 to Butter et al., a zeolite is incorporated with noble metal subsequent to zeolite crystallization but prior to catalyst extrusion. The catalyst is used for xylene isomerization at a temperature of 500° F. (260° C.) to 1000° F. (540° C.), a pressure between 50 and 1000 psig, a WHSV of 1 to 50 and a hydrogen/hydrocarbon mole ratio of 1 to 20.

Conversion of Oxygenates to Hydrocarbons

U.S. Pat. No. 4,476,330 to Kerr et al., which is herein incorporated by reference, describes the conversion of aliphatic oxygenates to a higher molecular weight compound by contacting with a zeolite having a silica/alumina ratio substantially greater than 10 at a temperature of 70° F. (21° C.) to 1400° F. (760° C.). The feeds include lower aliphatic organic oxygenates up to $C_6$, acetals, ketals, acid halides, alcohols, carboxylic acids, aldehydes, acid anhydrides, epoxides, ethers, esters, hemiacetals, gem diols, hydroxy acids, ketones, ketenes, lactones, peracids, peroxides, sugars, and especially alcohols, ethers and esters.

Oligomerization of olefins

The modified catalysts of the invention are advantageously used in the oligomerization of olefins to form gasoline, distillate, lube oils or chemicals in conversion reactions of the type described, for example, in U.S. Pat. Nos. 4,517,399, 4,520,221, 4,547,609 and 4,547,613 which are herein incorporated by reference.

U.S. Pat. No. 4,517,399 to Chester et al. describes the conversion of olefins of 3 to 18 carbons, e.g. propylene, to high viscosity, low pour point lubricating oils by contacting with ZSM-5 type zeolites having large crystals of at least two microns. The conversion conditions include a temperature of 350° F. (177° C.) to 650° F. (343° C.) a pressure of 100 to 5000 psig, and a WHSV of 0.1 to 10.

U.S. Pat. No. 4,520,221 to Chen describes the polymerization of olefins of 2 to 8 carbons, e.g. propylene, butylene, to high viscosity lubes, e.g. linear hydrocarbons, over highly siliceous, acidic ZSM-5 type catalysts with surface acidity inactivated by treatment with base, e.g. bulky amines with a cross-section larger than about 5 Angstroms. The conversion involves a one or two stage process with the polymerization of lower olefins to linear materials, e.g. at about 200° C. over a surface poisoned zeolite, and oligomerization of the product over a modified or unmodified catalyst at a temperature of 50°–75° lower than the first stage, e.g. 150° C. Therefore, the temperatures range from 25° C. to 400° C., with a pressure of atmospheric to 1500 psi and a WHSV of 0.04 to 1.0.

U.S. Pat. No. 4,547,609 to Dessau describes a two stage process whereby in the first stage, light olefins of 2 to 6 carbons are oligomerized to gasoline and distillate liquids including aliphatics of 10 to 20 carbons over a zeolite having a crystal size greater than 0.5 micron at conditions including at a temperature of 500° F. (260° C.) or higher, e.g. a range of 500° F. (260° C.) to 800° F. (437° C.), a pressure of atmospheric to 2000 psig and a WHSV of 0.1 to 20. In the second stage, the distillate fraction is converted to high viscosity lubes by contact with a zeolite of smaller crystal size under milder conditions of a temperature about 200° F. (100° C.) to 500° F.

(260° C.), a pressure of atmospheric to 650 psig, and a WHSV less than one.

U.S. Pat. No. 4,547,613 to Garwood et al. describes converting olefins of 2 to 16 carbons to high viscosity lube oil. A ZSM-5 type catalyst is pre-conditioned by contact with light olefins of 2 to 16 carbons, e.g. propylene at 400° F. (204° C.) to 1000° F. (538° C.), at a pressure of 0 to 100 psig for 1 to 70 hours. Conversion conditions include a temperature of 350° F. (177° C.) to 650° F. (343° C.), a pressure of 400 to 5000 psig and a WHSV of 0.1 to 10. The lube fraction may be subjected to a hydrogenation step to stabilize. Conversion of aromatics to dialkyl-substituted benzene The modified zeolite catalysts of the invention are advantageously used in the conversion of aromatics compounds to provide dialkyl-substituted benzene products which are highly enriched in the para-dialkyl substituted benzene isomer. Conversion reactions of this type include aromatics alkylation, transalkylation and disproportionation. Aromatics alkylations in which the catalysts of the invention can be used are described, for example, in U.S. Pat. Nos. 3,755,483, 4,086,287, 4,117,024 and 4,117,026 which are herein incorporated by reference.

As described in U.S. Pat. No. 3,755,483 to Burress, aromatic hydrocarbons such as benzenes, naphthalenes, anthracenes and substituted derivatives thereof, e.g. toluene and xylene, may be alkylated with alkylating agents such as olefins ethylene, propylene, dodecene, and formaldehyde, alkyl halides, and alkyl alcohols with 1 to 24 carbons under vapor phase conditions including a reactor inlet temperature up to about 900° F. (482° C.), with a reactor bed temperature up to about 1050° F. (566° ), at a pressure of about atmospheric to about 3000 psig, a ratio of aromatic/alkylating agent of about 1:1 to about 20:1 and a WHSV of 20 to 3000 over ZSM-12.

As described in U.S. Pat. No. 4,086,287 to Kaeding et al., monoalkylbenzenes having alkyls of 1-2 carbons, such as toluene and ethylbenzene, may be ethylated to produce a para-ethyl derivative, e.g. para-ethyltoluene at a temperature of from about 250° C. to about 600° C., a pressure of 0.1 atmospheres to 100 atmospheres, a weight hourly space velocity (WHSV) of 0.1 to 100, and a ratio of feed/ethylating agent of 1 to 10 over a catalyst having an acid activity, i.e., alpha, of 2 to 5000, modified by precoking or combining with oxides of phosphorus, boron or antimony to attain a catalyst with a xylene sorption capacity greater than 1 g/100 g of zeolite and an ortho xylene sorption time for 30% of said capacity of greater than 10 minutes, where sorption capacity and sorption time are measured at 120° C. and a xylene pressure of 4.5±0.8 mm of mercury.

U.S. Pat. No. 4,117,024 to Kaeding describes a process for the ethylation of toluene or ethylbenzene to produce p-ethyltoluene at a temperature of 350° C. to 550° C., a critical pressure of greater than one atmosphere and less than 400 psig, with hydrogen/ethylene ratio of 0.5 to 10 to reduce aging of the catalyst. The zeolite described in U.S. Pat. No. 4,117,024 has a crystal size greater then one micron, and is modified as the catalyst in U.S. Pat. No. 4,086,287 to attain the sorption capacity described in U.S. Pat. No. 4,086,287.

U.S. Pat. No. 4,117,026 to Haag and Olson describes the production of para-dialkyl benzenes having alkyls of 1 to 4 carbons under conditions which vary according to the feed. When the feed includes monoalkyl substituted benzenes having an alkyl of 1 to 4 carbons, olefins of 2 to 15, or paraffins of 3 to 60 carbons or mixtures thereof, conversion conditions include a temperature of 250° C. to 750°, a pressure of 0.1 to 100 atmospheres and a WHSV of 0.1 to 2000. For the disproportionation of toluene, the conditions include a temperature of 400° C. to 700° C., a pressure of 1 to 100 atmospheres and a WHSV of 1–50. When the feed includes olefins of 2 to 15 carbons including cyclic olefins, the conversion conditions include a temperature of 300° C. to 700° C., a pressure of 1 to 100 atmospheres and a WHSV of 1 to 1000. When the feed includes paraffins of 3 to 60 carbons, conditions include a temperature of 300° C. to 700° C., a pressure of 1 to 100 atmospheres and a WHSV of 0.1 to 100. However for lower paraffins of 3 to 5 carbons, the temperature should be above 400° C. When the feed includes mixed aromatics such as ethylbenzene and toluene, and also optionally olefins of 2 to 20 carbons or paraffins of 5 to 25 carbons, conversion conditions includes a temperature of 250° C. to 500° C. and a pressure greater than 200 psig. In the absence of added aromatics, the olefins and higher paraffins are more reactive and require lower severity of operation, e.g. a temperature of 250° C. to 600° C., preferably 300° -550° C. The catalyst described in U.S. Pat. No. 4,117,026 is modified as in U.S. Pat. No. 4,086,287.

Conversion of light paraffins and olefins to aromatics

The modified catalysts of the invention may also be used in the conversion of light paraffins and olefins to aromatics in processes of the type described, for example, in U.S. Pat. Nos. 3,760,024 and 3,756,942 which are herein incorporated by reference.

U.S. Pat. No. 3,760,024 to Cattanach describes a process for the conversion of paraffins of 2 to 4 carbons and/or olefins to aromatics of 6 to 10 carbons over a ZSM-5 type catalyst with or without hydrogenation/-dehydrogenation component. Conversion conditions include a temperature of 100° C. to 650° C., a pressure of 0 to 1,000 psig, a WHSV of 0.1 to 500 and a hydrogen/hydrocarbon ratio of 0 to 20.

U.S. Pat. No. 3,756,942 to Cattanach describes the conversion of paraffins, olefins and naphthenes to aromatics over ZSM-5 type catalysts. If the feed contains at least 35 wt. % olefins, conversion is at 650° F. (363° C.) to 1400° F. (760° C.). If the feed contains less than 35 wt. % olefins, the temperature is 900° F. (482° C.) to 1400° F. (760° C.) with the absence of substantial added hydrogen. For both types of feed, the pressure is atmospheric to 35 atmospheres and the WHSV 1 to 15.

Therefore, the modified catalysts of the present invention are suitable for use in a variety of shape selective hydrocarbon conversion processes including as non-limiting examples, cracking hydrocarbons with reaction conditions including a temperature of from about 300° C. to about 700° C., a pressure of from about 0.1 atmosphere (bar) to about 30 atmospheres and a weight hourly space velocity of from about 0.1 hr$^{-1}$ to about 20 hr$^{-1}$; dehydrogenating hydrocarbon compounds with reaction conditions including a temperature of from about 300° C. to about 700° C., a pressure of from about 0.1 atmosphere to about 10 atmospheres and weight hourly space velocity of from about 0.1 to about 20; converting paraffins to aromatics with reaction conditions including a temperature of from about 300° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting olefins to aromatics, e.g. benzene, toluene and xylene, with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting alcohols, e.g. methanol, or ethers, e.g. dimethylether, or mixtures thereof to hydrocarbons including olefins and/or aromatics with reaction conditions including a temperature of from about 275° C. to about 600° C., a pressure of from about 0.5 atmosphere to about 50 atmospheres and a liquid hourly space velocity of from about 0.5 to about 100; isomerizing xylene feedstock components with reaction conditions including a temperature of from about 230° C. to about 510° C., a pressure of from about 3 atmospheres to about 35 atmospheres, a weight hourly space velocity of from about 0.1 to about 200 and a hydrogen/hydrocarbon mole ratio of from about 0 to about 100; disproportionating toluene with reaction conditions including a temperature of from about 200° C. to about 760° C., a pressure from about atmospheric to about 60 atmospheres and a weight hourly space velocity of from about 0.08 to about 20; alkylating aromatic hydrocarbons, e.g. benzene and alkylbenzenes in the presence of an alkylating agent, e.g. olefins, formaldehyde, alkyl halides and alcohols, with reaction conditions including a temperature of from about 250° C. to about 500° C., a pressure of from about atmospheric to about 200 atmospheres, a weight hourly space velocity of from about 2 to about 2000 and an aromatic hydrocarbon/alkylating agent mole ratio of from about 1/1 to about 20/1; and transalkylating aromatic hydrocarbons in the presence of polyalkylaromatic hydrocarbons with reaction conditions including a temperature of from about 340° C. to about 500° C., a pressure of from about atmospheric to about 200 atmospheres, a weight hourly space velocity of from about 10 to about 1000 and an aromatic hydrocarbon/polyalkylaromatic hydrocarbon mole ratio of from about 1/1 to about 16/1.

In general, therefore, catalytic conversion conditions over a catalyst comprising the modified zeolite include a temperature of from about 100° C. to about 760° C., a pressure of from about 0.1 atmosphere to about 200 atmospheres, a weight hourly space velocity of from about 0.08 hr$^{-1}$ to about 2000 hr$^{-1}$ and a hydrogen/organic, e.g. hydrocarbon compound of from 0 to about 100.

Toluene Disproportionation

Toluene Disproportionation will be used as a representative shape selective conversion. A catalyst treated in the manner described herein has a desirable decreased ortho-xylene sorption rate parameter and yields a para-selective product in toluene disproportionation.

The modification method decreases o-xylene diffusivity of the catalyst. Decreasing o-xylene diffusivity increases para-selectivity. Diffusion rate constants in toluene disproportionation have been discussed by D.H. Olson and W.O. Haag, "Structure-Selectivity Relationship in Xylene Isomerization and Selective Toluene Disproportionation," Catalytic Materials Relationship Between Structure and Reactivity, ACS Symposium Ser. No. 248 (1984).

In toluene disproportionation, toluene diffuses into the zeolite with a diffusivity $D_T$. The toluene undergoes disproportionation to p-, m-, and o-xylene and benzene at a total rate constant $k_D$.

The degree of para-selectivity depends on the activity and the diffusion characteristics of the catalyst. The primary product will be rich in the para isomer if initially produced m- and o- xylene diffuse out of the zeolite crystal at a lower rate ($D_{m,o}/r^2$) than that of their conversion to p-xylene ($k_I$) and the p-xylene diffusion ($D_p/r^2$) out of the catalyst.

$D_m$ = diffusion of m-xylene
$D_o$ = diffusion of o-xylene
$D_p$ = diffusion of p-xylene
r = length of diffusion path (crystal radius)
$k_I$ = rate of interconversion via isomerization of xylene isomers yielding secondary xylene product m-xylene and o-xylene.

It is desirable to reduce the isomerization of p-xylene to o- and m-xylene in a secondary reaction by adjusting $D_{m,o}/r^2$ downward so that $$k_I > \frac{D_{m,o}}{r^2}$$

Thus a para-rich primary product will result. It is therefore apparent that if the m-or o-xylene diffusion rate can be adjusted downward, the p-xylene product will increase.

The invention involves the methylation of toluene. The methylation reaction of the present invention is described herein in terms of disproportionation. However, the present invention also applies to other methylation reactions such as those using methylhalides and methylethers.

Reaction conditions in the disproportionation include temperatures ranging from about 100° C. to about 600° C., preferably about 350° C. to about 600° C., more preferably from about 350° C. to about 540° C.; pressures ranging from about 0 to about 2000 psig, preferably from about 15 to about 800 psig; a mole ratio of hydrogen to hydrocarbons from about 0 (i.e. no hydrogen is present) to about 20, preferably about 0.1 to about 10, more preferably from about 1 to about 4; at a weight hourly space velocity (WHSV) from about 0.1 to about 100 hr$^{-1}$, preferably about 0.1 to about 20 hr$^{-1}$, more preferably from about 1 to about 10 hr$^{-1}$.

Normally a single pass conversion of a toluene stream results in a product stream which includes dimethylbenzenes having alkyl groups at all locations, i.e., ortho-, meta-, and para-xylenes. Furthermore, the xylenes are known to proceed in a reaction which produces unwanted ethylbenzenes (EB) by the following reaction:

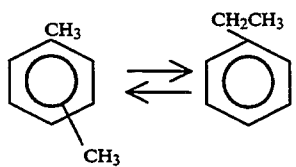

By deposition of platinum on the molecular sieve, the presence of ethylbenzene can be reduced.

The present invention, however, provides high efficiency conversion which reduces production of ortho- and meta-isomers to the benefit of the desired para-isomer. The resulting product stream can contain greater than a 90% purity of para-xylene.

As explained in greater detail herein, the present invention provides a process for obtaining para-xylene at toluene conversion rates of at least about 15%, preferably at least about 20-25%, and with para-xylene purity of greater than about 80%, preferably at least 90%.

The present invention also includes the regioselective conversion of toluene to para-xylene by methylating toluene in a reaction stream containing a toluene feed with a trim selectivated catalytic molecular sieve which is also preselectivated according to the modification method described above, with reaction conditions to provide a single pass, para-xylene selectivity of at least about 90% based on the total xylene products so that $$\text{p-xylene selectivity} = \frac{\text{g p-xylene}}{\text{g total xylene}} \times 100.$$

The trim selectivation methods are described below. By "pre-selectivating" a catalytic molecular sieve is meant modifying the molecular sieve so that a coating of silica extensively covers and resides substantially exclusively on the external surface of the molecular sieve.

By "trim selectivating" a catalytic molecular sieve is meant that a silicon-containing selectivating agent is cofed with toluene over the molecular sieve under toluene disproportionation conditions. As used herein, the term "para-xylene purity" means the percentage of para-xylene in all of the xylene products para-xylene, ortho-xylene, and meta-xylene. Those skilled in the art will appreciate that the proximity of the boiling points of these $C_8$ products necessitates more expensive separation processes whereas para-xylene may be more readily separated from other components in the product stream such as benzene, toluene, and para-ethyltoluene.

As used herein, the term "xylene product" or "xylene conversion product" indicates the total amount of xylenes resulting from the disproportionation reaction. The word "para-xylene" in this term is not intended to limit the scope of the present invention to the production of xylenes since other para-substituted aromatics may be produced.

The invention also comprises a method for the regioselective production of para-xylene by passing a reaction stream which contains an aromatic feedstock, e.g., toluene, in a single pass, over a trim-selectivated catalytic molecular sieve, which is pre-selectivated according to the modification method of the invention, the single pass in the presence of hydrogen at reaction conditions suitable to provide para-xylene selectivity based on total xylene product of greater than about 95%, preferably greater than about 99% and a para-xylene purity based on total $C_8$ products of greater than about 90%, preferably greater than about 98%. The product stream may also include small amounts of ortho- and meta-xylene and trace amounts of impurities such as ethylbenzene.

The toluene may be fed simultaneously with a second silicon source which is a high-efficiency selectivating agent, and hydrogen at reaction conditions until the desired p-xylene selectivity, e.g., 90%, is attained, whereupon the feed of selectivating agent is discontinued. This co-feeding of selectivating agent with toluene will be termed "trim selectivation". Reaction conditions for this trim-selectivation step generally include a temperature of about 50°-540° C. and a pressure of about atmospheric - 5000 psig. The feed is provided to the system at a rate of about 0.1-20 WHSV. The hydrogen is fed at a hydrogen to hydrocarbon molar ratio of about 0.1-20.

The high efficiency para-xylene selectivating agent for trim selectivation preferably comprises a silicon containing compound discussed in greater detail below. For example, organic silicons such as phenylmethyl silicone, dimethyl silicone, and mixtures thereof are suitable. According to one embodiment of the present invention, a silicone containing phenylmethylsilicone and dimethylsilicone groups in a ratio of about 1:1 is co-fed to the system, while the other components, e.g., toluene and hydrogen, are fed in the amounts set forth above. The high-efficiency para-xylene selectivating agent is fed in an amount of about 0.1-50% of the toluene according to this preferred embodiment. Depending upon the percentage of selectivating agent used, the trim selectivation will last for at least one hour, preferably about 1 to about 48 hours, most preferably less than 24 hrs.

The catalyst is "pre-selectivated" by ex situ modification with an amino silane selectivating agent, then calcined and subsequently may be "trim selectivated" with a high efficiency para-xylene selectivating agent.

As used herein, the term "high efficiency, p-xylene selectivating agent" as used for trim selectivation is used to indicate substances which will increase the para-selectivity of a catalytic molecular sieve to the stated levels in toluene disproportionation while maintaining commercially acceptable toluene to xylene conversion levels. Such substances include, for example, organic silicon compounds such as phenylmethyl silicone, dimethylsilicone, and blends thereof which have been found to be suitable.

The trim selectivation of the catalyst is preferably performed with a silicone containing compound. An example of silicone compounds which can be used in the present invention can be characterized by the general formula:

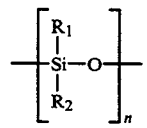

where $R_1$ is hydrogen, fluorine, hydroxy, alkyl, aralkyl, alkaryl or fluoro-alkyl. The hydrocarbon substituents generally contain from 1 to 10 carbon atoms and preferably are methyl or ethyl groups. $R_2$ is selected from the same group as $R_1$, and n is an integer of at least 2 and generally in the range of 3 to 1000. The molecular weight of the silicone compound employed is generally between about 80 and about 20,000 and preferably within the approximate range of 150 to 10,000. Representative silicone compounds include dimethylsilicone, diethylsilicone, phenylmethylsilicone, methylhydrogensilicone, ethylhydrogensilicone, phenylhydrogensilicone, methylethylsilicone, phenylethylsilicone, diphenylsilicone, methyltrifluoropropylsilicone, ethyltrifluoropropysilicone, polydimethylsilicone, tetrachlorophenylmethyl silicone, tetrachlorophenylethyl silicone, tetrachlorophenylhydrogen silicone, tetrachlorophenylphenyl silicone, methylvinylsilicone and ethylvinylsilicone. The silicone compound need not be linear but may be cyclic as for example hexamethylcyclotrisiloxane, octamethylcyclotetrasiloxane, hexaphenylcyclotrisiloxane and octaphenylcyclotetrasiloxane. Mixtures of these compounds may also be used as well as silicones with other functional groups. Other silicon-containing compounds, such as silanes, may also be utilized.

Preferably, the kinetic diameter of the high efficiency, p-xylene selectivating agent is larger than the zeolite pore diameter, in order to avoid reducing the internal activity of the catalyst.

Before trim-selectivation, the catalyst is preselectivated, and a silicon compound is deposited on the external surface of the catalyst.

While not wishing to be bound by theory, it is believed that the advantages of the present invention are in part obtained by protecting acid sites during preselectivation and by thereafter rendering acid sites on the external surfaces of the catalyst substantially inaccessible to reactants while increasing catalyst tortuosity. Acid sites existing on the external surface of the catalyst have been believed to isomerize the para-xylene exiting the catalyst pores back to an equilibrium level with the other two isomers thereby reducing the amount of para-xylene in the xylenes to only about 24%. By reducing the availability of these acid sites to the para-xylene exiting the pores of the catalyst, the relatively high level of para-xylene can be maintained. It is believed that the high-efficiency, p-xylene selectivity agents of the present invention block or otherwise render these external acid sites unavailable to the para-xylene by chemically modifying said sites.

In line with this theory, it is also believed that the presence of hydrogen in the reaction zone during the trim selectivation is important in order to maintain the desired high yields of para-xylene when a silicone compound is used as the high-efficiency para-xylene selectivating agent. The importance of the hydrogen may be reduced in alternative embodiments by using a high efficiency para-xylene selectivating agent comprising silane or some other compound which effectively renders the isomerizing acid sites on the external surface of the catalyst inaccessible.

The invention may utilize a high efficiency para-xylene selectivating agent which includes a silicon compound wherein the silicon compound is introduced by co-feeding, for example, at least one silicon compound with the toluene feedstock over a conversion catalyst at reaction conditions until the desired degree of selectivation is achieved, at which time the feed of selectivating agent may be discontinued.

The toluene feedstock preferably includes about 50% to 100% toluene, more preferably at least about 80% toluene in the toluene feedstock. Other compounds such as benzene, xylenes, and trimethylbenzene may also be present in the toluene feedstock without adversely affecting the present invention.

The toluene feedstock may also be dried, if desired, in a manner which will minimize moisture entering the reaction zone. Methods known in the art suitable for drying the toluene charge for the present process are numerous. These methods include percolation through any suitable desiccant, for example, silica gel, activated alumina, molecular sieves or other suitable substances, or the use of liquid charge dryers.

After pre-selectivation, the catalytic molecular sieves for the present invention are preferably converted to the hydrogen form and preferably comprise an intermediate pore-size zeolite such as a ZSM-5, ZSM-11, ZSM-22, ZSM-23, or ZSM-35. The crystal size of zeolites used herein is preferably greater than 0.1 micron.

For the improved disproportionation process of this invention, the suitable molecular sieve may be employed in combination with a support or binder material such as, for example, a porous inorganic oxide support or a clay binder. While the preferred binder is silica, other non-limiting examples of such binder materials include alumina, zirconia, magnesia, thoria, titanic, boria and combinations thereof, generally in the form of dried inorganic oxide gels. or gelatinous precipitates. Suitable clay materials include, by way of example, bentonite and kieselguhr. The relative proportion of suitable crystalline molecular sieve to the total composition of catalyst and binder or support may be about 30 to about 90 percent by weight and is preferably about 50–80 percent by weight of the composition. The composition may be in the form of an extrudate, beads or fluidizable microspheres.

Operating conditions employed in the improved process of the present invention may be adjusted to affect the para-selectivity and toluene conversion rate. Such conditions include the temperature, pressure, space velocity, molar ratio of the reactants, and the hydrogen to hydrocarbon mole ratio. One preferred embodiment of the present invention includes contacting a catalytic molecular sieve with a toluene feedstock which includes a silicone compound under conditions for effecting vapor-phase disproportionation. Conditions effective for accomplishing the high para-selectivity and acceptable toluene disproportionation conversion rates include a reactor inlet temperature of about 350°–600° C., preferably greater than about 350° C., a pressure of about atmospheric - 5000 psig, preferably about 100 to 1000 psig, a WHSV of about 0.1–20, preferably about 2–4, and a hydrogen to hydrocarbon mole ratio of about 0.1–20, preferably about 2–4. This process may be conducted in either batch or fluid bed operation with attendant benefits of either operation readily obtainable. The effluent may be separated and distilled to remove the desired product, i.e., para-xylene, plus other by-products.

The catalyst may be further modified in order to reduce the amount of undesirable by-products, particularly ethylbenzene. The state of the art is such that the reactor effluent from standard toluene disproportionation typically contains about 0.5% ethylbenzene by-product. Upon distillation of the reaction products, the level of ethyl-benzene in the $C_8$ fraction often increases to about 3–4 percent. This level of ethylbenzene is unacceptable for polymer grade p-xylene since ethylbenzene in the $C_8$ product, if not removed, degrades the quality of fibers ultimately produced from the p-xylene product. Consequently, ethylbenzene content must be kept low. The specification for ethylbenzene in the $C_8$ product has been determined by industry to be less than 0.3%. Ethylbenzene can be substantially removed by isomerization or by superfractionation processes. Removal of the ethylbenzene by conventional isomerization would be impractical with the present invention since the xylene stream, which includes greater than 90% para-xylene, would be concurrently isomerized to equilibrium xylenes reducing the amount of para-xylene in this xylene stream to about 24%. It is known in the art that the alternative procedure of removing the ethylbenzene by superfractionation is extremely expensive.

In order to avoid the need for downstream ethylbenzene removal, the level of ethylbenzene by-product is advantageously reduced by incorporating a hydrogenation-dehydrogenation function in the catalyst, such as by addition of a metal compound such as platinum. While platinum is the preferred metal, other metals such as palladium, nickel, copper, cobalt, molybdenum, rhodium, ruthenium, silver, gold, mercury, osmium, iron, zinc, cadmium, and mixtures thereof may be utilized. The metal may be added by cation exchange, in amounts of about 0.01–2%, typically about 0.5%. The metal must be able to enter the pores of the catalyst in order to survive a subsequent calcination step. For example, a platinum modified catalyst can be prepared by first adding the catalyst to a solution of ammonium nitrate in order to convert the catalyst to the ammonium form. The catalyst is subsequently contacted with an aqueous solution of tetraamine platinum(II) nitrate or tetraamine platinum(II) chloride. The metallic compound advantageously enters the pores of the catalyst. The catalyst can then be filtered, washed with water and calcined at temperatures of about 250° to 500° C.

By the present process, toluene can be converted to aromatic concentrates of high value, e.g., about 99% paraxylene based on all $C_8$ products. In a typical embodiment of the present process, optimum toluene conversion is found to be about 20–25 weight percent with a para-xylene purity of about 90–99%.

The following non-limiting examples illustrate the invention:

EXAMPLE 1

Selectivation of HZSM-5/$SiO_2$

A propylamine silane polymer (Hydrosil 2627, Hüls America, Inc.) was diluted with DI (deionized) $H_2O$ at a 1:1 weight ratio. HZSM-5/$SiO_2$, Si/$Al_2$=26:1 was treated with the silane polymer/$H_2O$ solution by impregnation for overnight. The sample was then calcined at 538° C. in nitrogen followed by air. A small amount of calcined material was exchanged with 1 M $NH_4NO_3$ at room temperature to determine the number of framework aluminum sites which remain after selectivation. The parent HZSM-5/$SiO_2$ material contained 0.76 meq/g acid sites while the selectivated material contained 0.29 meq/g acid sites in the crystalline framework.

Selectivation of NH4-ZSM-5/$SiO_2$ 10 grams of HZSM-5/$Si_2$, Si/$Al_2$=26:1, were exchanged with 1 M $NH_4NO_3$ at room temperature for one hour until at least 75% of the framework aluminum sites are exchanged with $NH_4+$ cations as measured by $NH_3$-TPAD.

The propylamine silane polymer as in Example 1 was diluted with DI $H_2O$ at a 1:1 ratio. The $NH_4$-ZSM-5/$SiO_2$ was then treated with the silane/$H_2O$ solution by impregnation for overnight. The sample was then calcined at 538° C. in nitrogen followed by air. A small amount of calcined material was exchanged with 1 M $NH_4NO_3$ at room temperature to determine the number of framework aluminum sites which remained after selectivation. The number of acid sites had decreased from 0.76 to 0.22 meq/g.

EXAMPLE 3

Selectivation of organic cation-containing ZSM-5/$SiO_2$ 10 grams of HZSM-5/$SiO_2$($SiO_2$/$Al_2O_3$=26:1, 65/35), were exchanged with a 2% n-propylamine/$H_2O$ solution at room temperature for one hour until at least 75% of the framework aluminum sites are exchanged with n-propylamine (n-pa) cations measured by $NH_3$-TPAD.

The propylamine silane polymer as in Example 1 was diluted with DI $H_2O$ at a 2:1 weight ratio. n-pa-ZSM-5/$SiO_2$ was then treated with the amino silane polymer/$H_2O$ solution by impregnation for overnight. The sample was then calcined at 538° C. in nitrogen followed by air. A small amount of calcined material was exchanged with 1 M $NH_4NO_3$ at room temperature to determine the number of framework aluminum sites which remained after selectivation. The number of acid sites decreased from 0.71 meq/g to 0.39 meq/g.

EXAMPLE 4

Selectivation of Na-ZSM-5/$SiO_2$ 10 grams of HZSM-5/$SiO_2$, Si/$Al_2$=26:1, were exchanged twice with 650 ml of 0.012N NaOH at room temperature for one hour. To examine the extent of sodium exchange, 0.1 g of NaZSM-5/$SiO_2$ was treated with $NH_3$ gas then refluxed in DI $H_2O$ for one hour, filtered and dried at 130° C. The number of acid sites not exchanged with a sodium cation was 0.017 meq/g.

The propylamine silane polymer as in Example 1 was diluted with DI $H_2O$ at a 2:1 weight ratio. Na-ZSM-5/$SiO_2$ was treated with the silane polymer/$H_2O$ solution by column exchange. The sample was then calcined at 538° C. in nitrogen followed by air to yield a $SiO_2$-ZSM-5/$SiO_2$ catalyst. The calcined material was exchanged with 1 M $NH_4NO_3$ at room temperature to determine the number of acid sites which remained after selectivation. $NH_3$-TPAD showed 0.62 meq/g of acid sites remained compared to 0.76 meq/g prior to selectivation.

Examples 1–4 demonstrate that to maintain a high number of acid sites it is necessary to protect the acid sites, preferably with a cation such as $Na^+$ or an organic cation rather than $H^+$ or $NH_4^+$. It is preferable to exchange greater than 75%, most preferably greater than 90%, of acid sites with $Na^+$ or an organic cation.

EXAMPLE 5

A $SiO_2$-ZSM-5/$SiO_2$ was prepared as in Example 4. The product had an o-xylene diffusivity of $5 \times 10^{-7} s^{-1}$ and an activity of 0.36 meq/g acid sites. The low number of acid sites is a result of incomplete sodium exchange of HZSM-5/$SiO_2$.

EXAMPLE 6

HZSM-5/$SiO_2$ was exchanged twice with 0.012N NaOH at room temperature for one hour. To determine the extent of sodium exchange, 0.1 g of NaZSM-5/$SiO_2$ was treated with $NH_3$ gas then refluxed in DI $H_2O$ for one hour, filtered and dried at 130° C. There were 0.02 meq/g catalyst unexchanged sites after sodium hydroxide exchange. This sodium exchanged silica bound catalyst was then given two treatments with an amino silane polymer.

First Selectivation

A propylamine silane polymer was diluted with DI $H_2O$ at a 1:1 ratio. For 10 grams of Na-ZSM-5/$SiO_2$, 5 grams of propylamine silane polymer as in Example 1 were diluted with 5 grams DI $H_2O$. 10 grams of Na-ZSM-5/$SiO_2$ were treated with 10 grams of the propylamine silane polymer/$H_2O$ solution by impregnation for overnight and then dried at 130° C.

The sample was then calcined in 300 cc/min N$_2$ using a heating rate of 2° C./min to 538° C. then held at 538° C. for 2 hours followed by 300 cc/min air heated at 2° C./min from 300° C. to 538° C. then held for 2 hours.

The o-xylene diffusivity was measured at 120° C. The selectivation procedure reduced the D/r$^2$ from 1.5×10$^{-4}$ s$^{-1}$ to 1×10$^{-5}$ s$^{-1}$. To reduce the diffusivity further a second selectivation was performed.

Second Selectivation 7 grams of propylamine silane polymer were diluted with 3 grams DI H$_2$O. 10 grams of SiO$_2$/Na-ZSM-5/SiO$_2$ prepared in the first selectivation were treated with 10 grams of the propylamine silane polymer/H$_2$O solution by impregnation for overnight and then dried at 130° C. The sample was N$_2$/air calcined as described above.

The calcined sample was exchanged 2–3 times with 1 M NH$_4$NO$_3$ at room temperature for 1–2 hours to reduce the sodium content to less than 500 ppm. The o-xylene diffusivity was 8×10$^{-7}$ s$^{-1}$. NH$_3$-TPAD found 0.61 meq/g of acid sites in the selectivated catalyst.

EXAMPLES 7–20

In Examples 7–20, catalytic evaluation of selectivated catalysts of Example 5 and Example 6 was conducted in an automated unit with on-line sampling. The products of Examples 5 and 6 were air calcined at 538° for two hours to convert the ammonium form to the hydrogen form, SiO$_2$-HZSM-5/SiO$_2$. One gram of 14/30 mesh product was loaded into a 0.305" stainless steel tube reactor. The sample was heated to 446° C. in 40 cc/min H$_2$ at a heating rate of 3.5° C./min. Pure toluene was then introduced at 446° C., 4, 8, 16 and 32 WHSV, 2 H$_2$/HC and 500 psi to measure the TDP rate constant. A solution of 1 wt.% phenylmethyl-dimethyl silicone copolymer (Dow 550) in toluene was then passed over the catalyst at 466° C., 4 WHSV, 2H$_2$/HC and 500 psi for 4–24 hours. The product selectivities are shown in Tables 1–3. To determine the activity/selectivity performance of the selectivated catalysts, reactor temperature and toluene WHSV were varied to change toluene conversion.

The results of the catalysis over the product of Example 5 are shown in Table 1 below:

TABLE 1

| | Example* | | | |
|---|---|---|---|---|
| | 7 | 8 | 9 | 10 |
| Temp, °C. | 446 | 446 | 468 | 468 |
| WHSV | 4 | 2 | 4 | 3 |
| Pres, psi | 500 | 500 | 500 | 500 |
| H$_2$/HC | 2 | 2 | 2 | 2 |
| Toluene Conv., % | 11.1 | 19.0 | 20.1 | 25.2 |
| p-xylene sel., % | 95.1 | 88.2 | 88.3 | 86.6 |
| p-xylene purity, % | 93.3 | 85.4 | 85.3 | 83.4 |

*10 hour in situ trim with 1% phenylmethyl silicone in toluene.

$$\text{p-xylene selectivity} = \frac{\text{wt. \% p-xylene}}{\text{total wt. \% xylenes}}$$

$$\text{p-xylene purity} = \frac{\text{wt. \% p-xylene}}{\text{total wt. C}_8 \text{ products}}$$

The results of catalysis over the product of Example 6 are shown in Tables 2 and 3 below.

TABLE 2

| | Example* | | | | |
|---|---|---|---|---|---|
| | 11 | 12 | 13 | 14 | 15 |
| Temp, °C. | 447 | 446 | 446 | 466 | 466 |
| WHSV | 8 | 8 | 16 | 8 | 16 |
| Pres, psi | 500 | 500 | 500 | 500 | 500 |

TABLE 2-continued

| | Example* | | | | |
|---|---|---|---|---|---|
| | 11 | 12 | 13 | 14 | 15 |
| H$_2$/HC | 2 | 2 | 2 | 2 | 16 |
| Toluene Conv., % | 19.2 | 23.8 | 11.6 | 25.8 | 17.0 |
| p-xylene sel., % | 93.0 | 93.0 | 96.5 | 90.7 | 93.7 |
| p-xylene purity, % | 90.1 | 88.5 | 94.7 | 86.3 | 90.8 |

*6 hour in situ trim with 1% phenylmethyl silicone in toluene.

TABLE 3

| | Example* | | | | |
|---|---|---|---|---|---|
| | 16 | 17 | 18 | 19 | 20 |
| Temp, °C. | 446 | 446 | 446 | 466 | 466 |
| WHSV | 4 | 8 | 16 | 4 | 8 |
| Pres, psi | 500 | 500 | 500 | 500 | 500 |
| H$_2$/HC | 2 | 2 | 2 | 2 | 2 |
| Toluene Conv., % | 20.1 | 14.2 | 9.0 | 26.3 | 18.4 |
| p-xylene sel., % | 93.3 | 94.8 | 97.2 | 91.4 | 93.2 |
| p-xylene purity, % | 90.4 | 92.8 | 95.8 | 90.8 | 90.0 |

*15 hour in situ trim with 1% phenylmethyl silicone in toluene.

The results show that using a catalyst pre-selectivated according to the invention, it is possible to achieve high para-xylene selectivity and high conversion rate at lower temperatures or higher WHSV compared to catalysts pre-selectivated after incomplete sodium exchange into the catalyst. Lower p-xylene selectivity was observed for the catalyst of Example 5 probably because of acid activity (or number of acid sites) was reduced during selectivation.

EXAMPLES 21–22

Effect of Steaming SiO$_2$ Selectivated Catalysts

NaZSM-5/SiO$_2$ was treated with a propylamine silane polymer/H$_2$O mixture, 7:1 wt ratio, at room temperature for overnight. The sample was filtered and dried at 130° C. and then N$_2$/air calcined as described above.

The calcined sample was exchanged 2–3 times with 1 M NH$_4$NO$_3$ at room temperature for 1–2 hours. The o-xylene diffusivity was 3×10$^{-7}$ s$^{-1}$. NH$_3$-TPAD determined the number of acid sites to be 0.43 meq/g.

The exchanged SiO$_2$-ZSM-5/SiO$_2$ material, was calcined in air at 538° C. and then steamed at 315° C. for 3 hours in 100% steam.

The catalytic performance of this steamed-selectivated SiO$_2$-ZSM-5/SiO$_2$ material was tested as in Examples 7–20. The results are shown in Table 4.

TABLE 4

| | Example* | |
|---|---|---|
| | 21 | 22 |
| Temp, °C. | 446 | 466 |
| WHSV | 4 | 4 |
| Pres, psi | 500 | 500 |
| H$_2$/HC | 2 | 2 |
| Toluene Conv., % | 15.5 | 27.1 |
| p-xylene sel. % | 96.9 | 91.4 |
| p-xylene purity, % | 94.7 | 87.9 |

*4 hour in situ trim with 1% phenylmethyl silicone in toluene.

EXAMPLE 23

One gram of water soluble propylamine silane polymer was diluted with one gram water. One gram of as-synthesized NaZSM-5 was mixed with this solution at room temperature for two hours. The sample was dried at 130° C. then calcined in nitrogen followed by air at 538° C.

The o-xylene sorption parameter $D/r^2$ was measured at 120° C. before and after the silane treatment. The $D_o/r^2$ decreased from $8.5\times10^{-6} s^{-1}$ before treatment to $6.5\times10^{-7} s^{-1}$ after treatment.

EXAMPLE 24

Non-Trim-Selectivated Toluene Disportionation

The modified HZSM-5 prepared in Example 23 was calcined and converted to hydrogen form and tested for toluene disproportionation. One atmosphere toluene was reacted with the treated HZSM-5 at 482° C. The conversion was changed by varying the WHSV. An unmodified HZSM-5 was similarly tested for toluene disproportionation.

The unmodified HZSM-5 showed 32.4% p-xylene selectivity at 4% toluene conversion with a rate constant ($k_D$) of 189. The modified HZSM-5 showed 42.9% p-xylene selectivity at 4% toluene conversion with a rate constant ($k_D$) of 105.

EXAMPLE 25

The modified HZSM-5 prepared in Example 23 was steamed at 650° F. and 100% $H_2O(g)$ for three hours. The o-xylene sorption parameter $D/r^2$ was measured. The $D/r^2$ had decreased from $6.5\times10^{-7} s^{-1}$ to $1.85\times10^{-7}$ after the steam treatment.

EXAMPLE 26

The steamed modified HZSM-5 prepared in Example 25 was tested for toluene disproportionation as in Example 24. The results showed 73.2% p-xylene selectivity at 4% toluene conversion with a rate constant ($k_D$) of 150.

EXAMPLES 27-29

A catalyst was sodium exchanged and twice selectivated with amino silane polymer followed by calcination and $NH_4NO_3$ exchange as described in Example 6.

The o-xylene diffusivity was $2\times10^{-7} s^{-1}$. $NH_3$-TPAD found 0.62 meq/g of acid sites in the selectivated catalyst.

Catalytic evaluation of the selectivated catalyst was carried out as described in Examples 7-20 with trim selectivation. The results after feeding of 1 wt % phenylmethyl-dimethyl silicone copolymer in toluene for 9 hours are shown in Table 5 below.

TABLE 5

|  | Examples | | |
| --- | --- | --- | --- |
|  | 27 | 28 | 29 |
| Temp, °C. | 466 | 466 | 466 |
| WHSV | 4 | 4 | 4 |
| Pres, psi | 500 | 500 | 500 |
| H2/HC | 2 | 2 | 2 |
| Toluene Conv., % | 20.1 | 23.1 | 24.8 |
| p-xylene sel. % | 96.3 | 95.6 | 95.3 |
| p-xylene purity, % | 92.6 | 91.6 | 91.0 |

What is claimed is:

1. A process for a shape selective hydrocarbon conversion comprising contacting a reaction stream comprising hydrocarbon to be converted, under conversion conditions, with a catalytic molecular sieve which has been modified by treatment with an amino silane polymer while molecular sieve acid sites are protected by association with at least one member of a group consisting of alkali metal, alkaline earth metal and organic cations.

2. The process of claim 1 wherein the shape selective hydrocarbon conversion is selected from a group consisting of dewaxing of paraffins, disproportionation of aromatics, transalkylation of alkylaromatics, isomerization of alkylaromatics, oligomerization of olefins, alkylation of aromatics, conversion of paraffins and olefins to aromatics and conversion of oxygenates to hydrocarbons.

3. The process of claim 1 wherein the conversion conditions comprise a temperature of from about 100° C. to about 760° C., a pressure of about 0.1 atmosphere to about 200 atmospheres, a weight hourly space velocity of from about 0.08 $hr^{-1}$ to about 2000 $hr^{-1}$ and a hydrogen/hydrocarbon molar ratio of from about 0 to about 100.

4. The process of claim 1 wherein the shape selective hydrocarbon conversion is toluene disproportionation.

5. The process of claim 1 wherein the molecular sieve comprises a zeolite having an initial Constraint Index from about 1 to about 12.

6. The process of claim 1 wherein after being modified, the molecular sieve is ion exchanged to contain ions selected from a group consisting of hydrogen, hydrogen precursor, metals of Periodic Table Group VIII and combinations thereof.

7. The process of claim 1 wherein the amino silane polymer is in substantially aqueous solution.

8. The process of claim 1 wherein the amino silane polymer is represented by the formula:

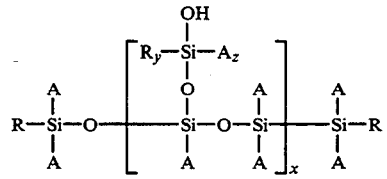

wherein

R is a $C_{1-6}$ alkane

A is selected from a group consisting of ethylamine, n-propylamine, iso-propylamine, n-butylamine or iso-butylamine x is 1-50 y is 0-2 z is 0-2 y+z=2.

9. The process of claim 1 wherein the molecular sieve is modified in an as-synthesized condition.

10. A process for disproportionation of toluene to xylene and benzene comprising:
contacting a reaction stream which comprises toluene, under reaction conditions for converting toluene to p-xylene, with a modified catalytic molecular sieve wherein the catalytic molecular sieve has been modified by treatment with an amino silane polymer while molecular sieve acid sites are protected by association with at least one member of a group consisting of alkali metal, alkaline earth metal and organic cations.

11. The process of claim 10 wherein the reaction conditions comprise a temperature from about 100° C. to about 600° C., a pressure from about 0 to about 2000 psig, a weight hourly space velocity (WHSV) between about 0.1 hr$^{-1}$ and about 100 hr$^{-1}$, and a hydrogen/hydrocarbon mole ratio from 0 to about 20.

12. The process of claim 10 wherein the molecular sieve comprises a zeolite having an initial Constraint Index from about 1 to about 12.

13. The process of claim 10 wherein after being modified, the catalytic molecular sieve is ion exchanged to contain ions selected from a group consisting of hydrogen, hydrogen precursor, metals of Periodic Table Group VIII and combinations thereof.

14. The process of claim 10 wherein the amino silane polymer is in substantially aqueous solution.

15. The process of claim 10 wherein the amino silane polymer is represented by the formula:

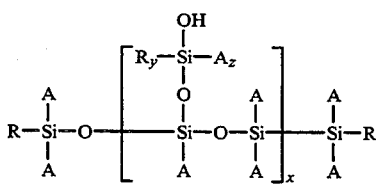

wherein

R is a C$_{1-6}$ alkane

A is selected from the group consisting of ethylamine, n-propylamine, iso-propylamine, n-butylamine or iso-butylamine x is 1-50 y is 0-2 z is 0-2 y+z=2.

16. The process of claim 10 wherein the molecular sieve is modified in an as-synthesized condition.

17. The process of claim 10 wherein the reaction stream further comprises a second silicon-containing compound which is a high efficiency para-xylene selectivating agent.

18. The process of claim 10 wherein the second silicon-containing compound is fed with the reaction stream for at least one hour.

19. The process of claim 10 wherein the high efficiency para-xylene selectivating agent comprises a silicone compound.

20. The process of claim 19 wherein the silicone compound comprises a mixture of phenylmethylsilicone and dimethylsilicone.

21. The process of claim 20 wherein the reaction stream comprises at least 80% toluene and at least 0.1% silicone compound.

22. The process of claim 17 wherein the contacting provides a single pass para-xylene selectivity relative to all xylene products of at least about 85% with at least about 15% toluene conversion.

* * * * *